United States Patent [19]

Norton et al.

[11] Patent Number: 5,021,065
[45] Date of Patent: Jun. 4, 1991

[54] ROTATIONALLY ACTUATED PROSTHETIC HELPING HAND

[75] Inventors: William E. Norton; Jewell G. Belcher, Jr.; James R. Carden; Thomas W. West, all of Huntsville, Ala.

[73] Assignee: The United States of America as represented by the Administrator, National Aeronautics and Space Administration, Washington, D.C.

[21] Appl. No.: 508,154

[22] Filed: Apr. 12, 1990

[51] Int. Cl.⁵ ............................ A61F 2/58; A61F 2/68
[52] U.S. Cl. ......................................... 623/63; 623/62
[58] Field of Search ................................... 623/61–65, 623/57

[56] References Cited

U.S. PATENT DOCUMENTS

| | | | |
|---|---|---|---|
| 2,268,951 | 1/1942 | McElroy | 623/61 |
| 2,347,909 | 5/1944 | Jarrett | 623/63 X |
| 2,349,411 | 5/1944 | Dorrance | 623/63 X |
| 2,382,404 | 8/1945 | Eberle | 623/63 |
| 2,408,880 | 10/1946 | Rebers | 623/63 |

Primary Examiner—Ronald Frinks
Attorney, Agent, or Firm—Jerry L. Seemann; Robert L. Broad, Jr.

[57] ABSTRACT

A prosthetic device for below-the-elbow amputees having a cuff, a stem, a housing, two hook-like fingers, an elastic band for holding the fingers together, and a brace. The fingers are pivotally mounted on a housing that is secured to the amputee's upper arm with the brace. The stem, which also contains a cam, is rotationally mounted within the housing and is secured to the cuff, which fits over the amputee's stump. By rotating the cammed stem between the fingers with the lower arm, the amputee can open and close the fingers.

13 Claims, 5 Drawing Sheets

Section 2-2

Section 1-1

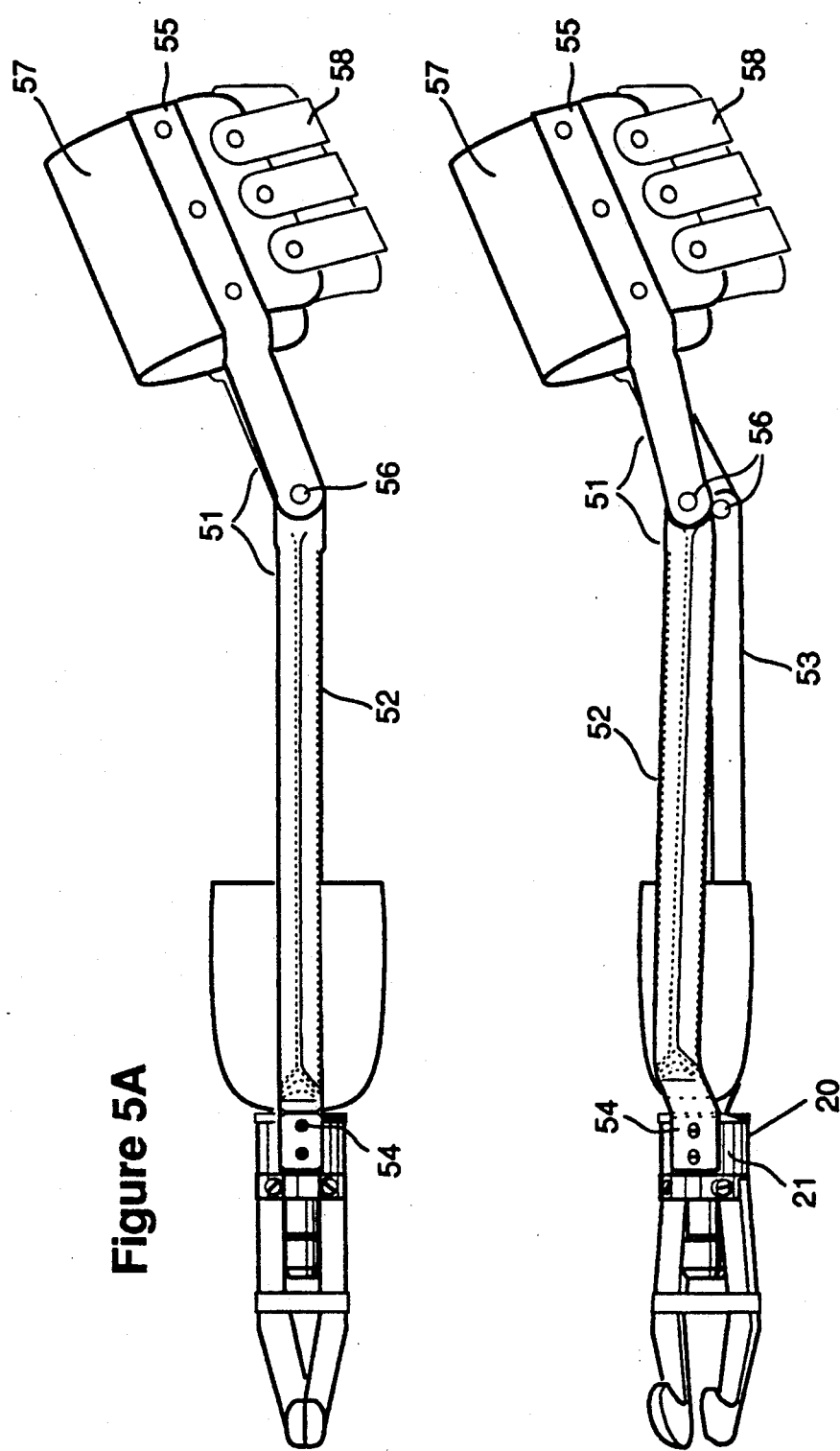

ROTATIONALLY ACTUATED PROSTHETIC HELPING HAND

ORIGIN OF THE INVENTION The invention described in this patent application was made in the performance of work under a NASA contract and is subject to the provisions of Public Law 96-517 (94 Stat 3019; 35 U.S.C. 200-211).

BACKGROUND OF THE INVENTION

Field of the Invention

This invention relates to a prosthetic device. Specifically, the present invention pertains to a prosthetic helping hand for use by below-the-elbow amputees. This prosthetic hand contains a clamping mechanism that is opened and closed by rotation of the lower arm.

Background Information

Prosthetic devices used to assist people who have received a below-the-elbow arm amputation generally fall into to two categories: bionic devices and body-powered devices. The body-powered devices seem to be the most preferred alternative. Many of the current artificial limbs have disadvantages which consist of being (1) uncomfortable, (2) not very durable, (3) heavy, (4) bulky, or (5) awkward to use. These problems are exacerbated for those persons who are very active. The present invention overcomes these disadvantages by providing a simple, easy-to-operate prosthetic helping hand with improved comfort and durability.

SUMMARY OF THE INVENTION

The present invention has the ability to assist below-the-elbow amputees in performing a variety of tasks. This prosthetic hand comprises a clamping mechanism that is attached to the stump and is operated by rotation of the lower arm. The clamping mechanism is used to assist in those functions that would otherwise be performed by the hand.

An object of this invention is to provide a prosthetic device for a person whose arm has been amputated below the elbow.

Another object of this invention is to provide a prosthetic hand with a clamping mechanism which can simulate the work of the thumb against the fingers.

Still another object of this invention is to provide a prosthetic hand which can be operated by the rotational movement of the lower arm.

BRIEF DESCRIPTION OF THE DRAWINGS

Further details of the present invention are explained below with the help of the attached drawings in which:

FIGS. 5A and 5B represent perspective views of the invention in fully assembled form. FIG. 5A shows the invention with closed fingers and FIG. 5B shows the invention with open fingers.

DESCRIPTION OF THE PREFERRED EMBODIMENT

A preferred embodiment of the present invention comprises a cuff, a stem, a housing, a first finger, a second finger, a means for biasing the fingers towards each other, and a brace.

Figure 1B:
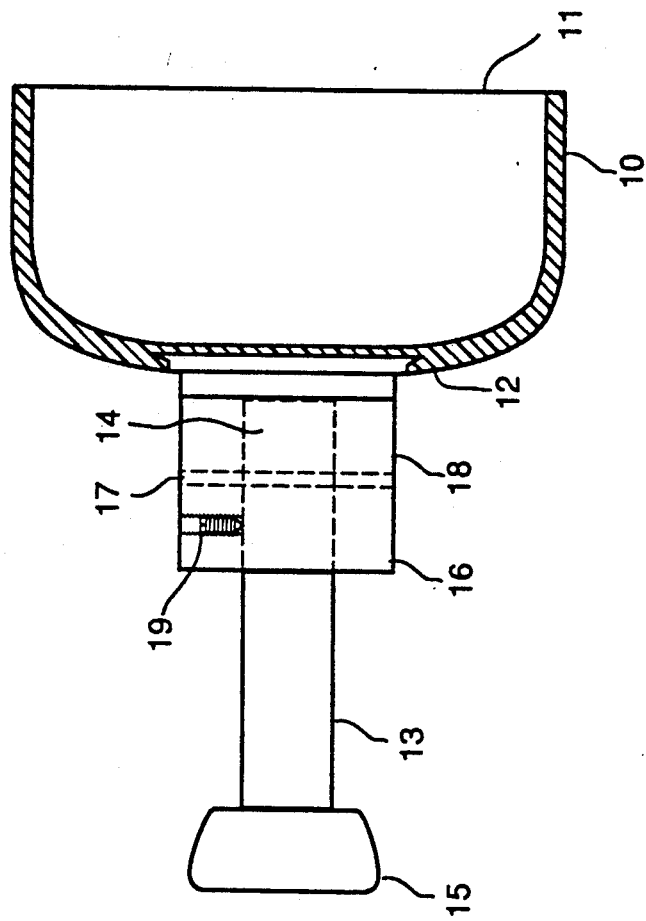
FIGS. 1A and 1B represent an end view and a side view, respectively, of the cuff and stem assembly belonging to this invention.
Figure 1A:
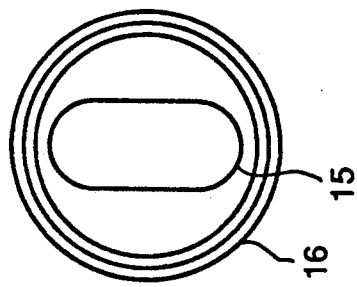
Figure 2B:
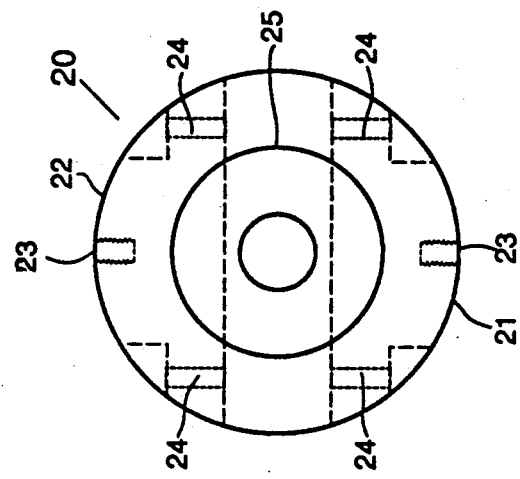
FIGS. 2A, 2B and 2C represent a side view, right end view, and left end view, respectively, of the housing belonging to this invention.
Figure 2A:
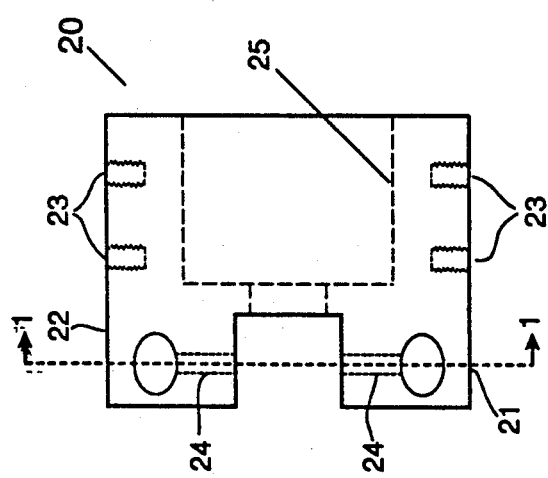
Figure 2C:
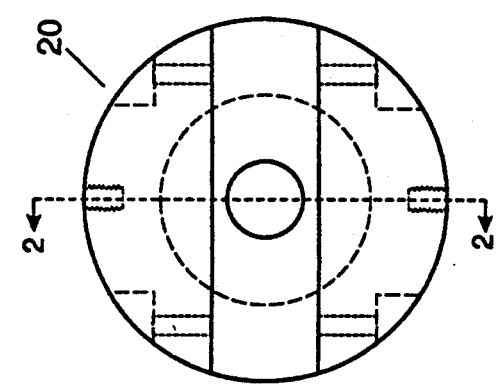
Figure 2E:
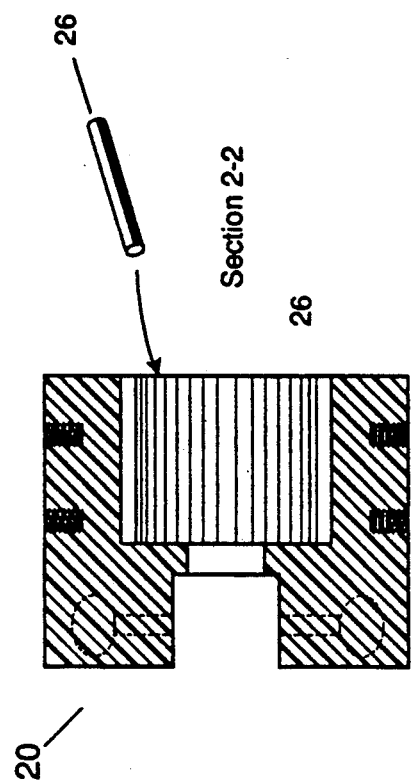
FIGS. 2D and 2E are sectional views of the housing.
Figure 2D:
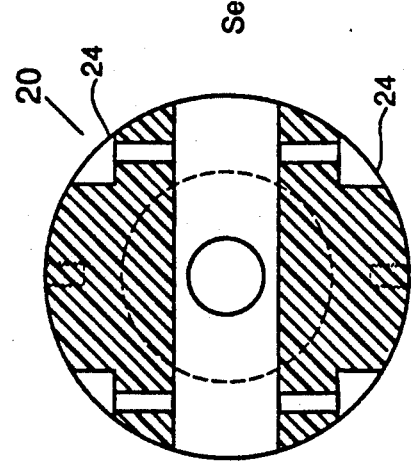

FIGS. 1A and 1B show a cuff 10 having an open end 11 and a closed end 12. The cuff 10 fits over the stump of an amputee's arm and is usually custom made to provide an individual fit. A stem 13 having a plain end 14 and a cam end 15 is attached to the closed end 12 of the cuff 10. In the embodiment shown, the stem 13 is attached to the cuff 10 by a cylindrical anchor 16 which is affixed to the cuff 10. The cylindrical anchor 16 may be cast directly into the cuff 10 during fabrication of the cuff 10. The plain end 14 of the stem 13 is secured within the anchor 16 by a pin 17. Thus, the cuff 10 and stem 13 are able to act together as a single unit. Alternatively, the stem 13 may be secured within the cylindrical anchor 16 by a set screw 19 which is threaded through the anchor 16 and against the plain end 14 of the stem 13. This latter alternative has the advantage of allowing the position of the cam end 15 to be adjusted relative to the cuff 10. The cylindrical anchor further has an outer surface 18 which may serve as a bearing race.

FIGS. 2A, 2B, 2C, 2D and 2E show a housing 20 having two opposite sides 21, 22. The two opposite sides 21, 22 have threaded holes 23 for securing a brace 51 (see FIG. 5A) to the housing 20. The opposite sides 21, 22 containing the threaded holes 23 do not have to be located as shown. The desired orientation of the housing 20 relative to the brace 51 will determine the location of the opposite sides 21, 22 and the threaded holes 23. The housing 20 also has locations 24 for pivotally mounting a finger 30 (see FIGS. 3A, 3B and 3C) to the housing 20. In the embodiment shown, the housing 20 has an inner surface 25 which aligns with the outer surface 18 of the cylindrical anchor 16. The inner surface 25 of the housing 20 may also serve as a bearing race. Thus, roller bearings 26 (see FIG. 2E) may be used between the outer surface 18 of the cylindrical anchor 16 and the inner surface 25 of the housing 20. The roller bearings 26 facilitate rotation of the stem 13 within the housing 20.

Figure 3C:
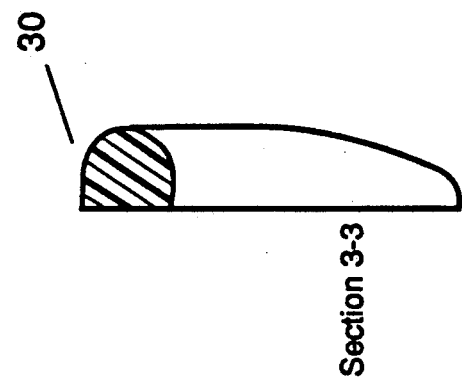
FIGS. 3A, 3B and 3C represent a top view, side view and partial sectional view, respectively, of the fingers belonging to this invention.
Figure 3A:
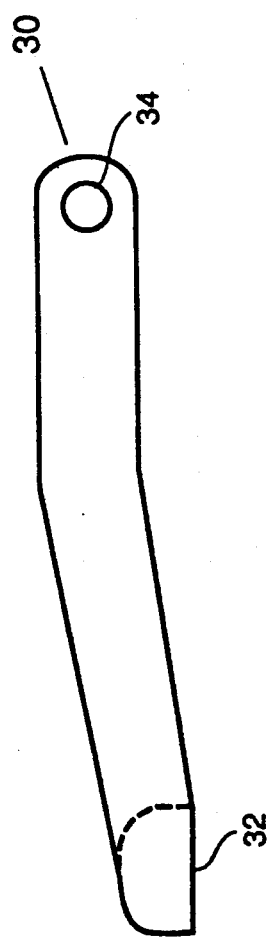
Figure 3B:
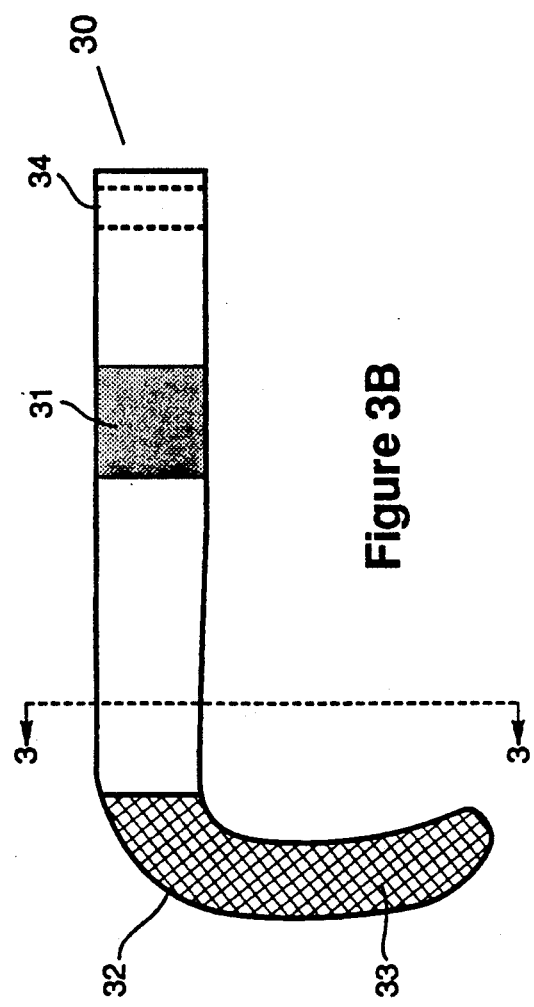

FIGS. 3A, 3B and 3C show a finger 30 having a bearing surface 31 and a clamping end 32. The clamping end 32 may have a roughened surface 33 to provide better gripping capability to the finger 30. A location 34 is provided so that the finger 30 may be pivotally mounted.

Figure 4:
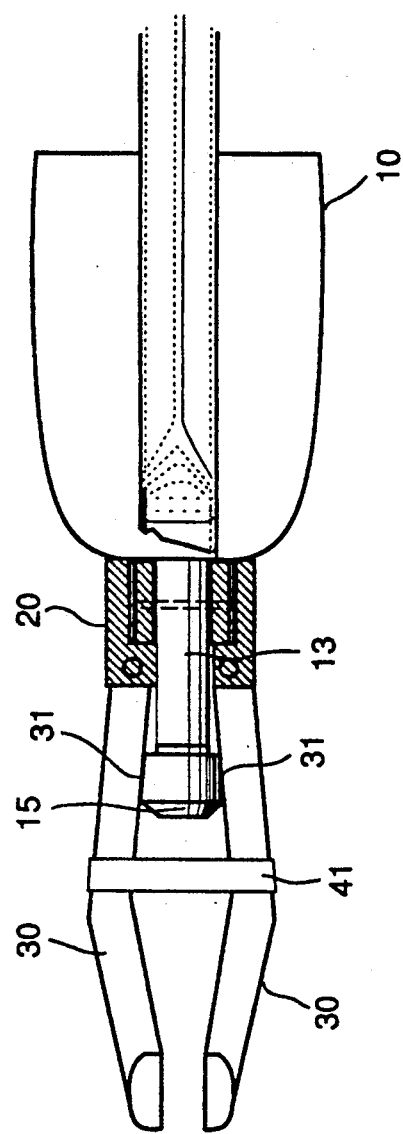
FIG. 4 represents an enlarged view of the cuff, stem, housing, and fingers in assembled form with the housing shown in section.

FIG. 4 shows the housing 20 pivotally mounted on the cuff 10 and stem 13 assembly and shows the two fingers 30 pivotally mounted to the housing 20. In the embodiment shown, the bearing surfaces 31 of the fingers 30 are held against the cam end 15 of the stem 13 by an elastic band 41 which is wrapped around the fingers 30. An alternative to the elastic band 41 would be a spring mechanism (not shown) mounted between the fingers 30 that would hold the fingers 30 against the cam end 15 of the stem 13.

FIGS. 5A and 5B show the invention in its fully assembled form. As shown in the figures, a brace 51 is attached to the opposite sides 21, 22 of the housing 20. The brace 51 consists of a first bar 52 and a second bar 53. Each of the two bars 52, 53 have two ends 54, 55 with a pivot 56 between the two ends 54, 55. The pivots 56 are aligned with each other so that they coincide with the location of the wearer's elbow. Attached to the ends 55 of the bars 52, 53 is an adjustable wraparound 57. The adjustable wraparound 57 may contain a nylon fabric 58 which can be fastened to itself (e.g., VEL-CRO) for securing the wraparound 57 to the upper arm. Ends 54 of the brace 51 are secured to the housing 20, preferably with screws.

The present invention is utilized by placing an arm which has been amputated below the elbow into the cuff. The adjustable wraparound is then secured to the upper arm. The housing is thus held stationary with respect to the upper arm by the brace which connects the wraparound to the housing. When the lower arm is rotated, the cuff and stem assembly rotate with respect to the housing. Since the elastic band holds the fingers against the cam end of the stem, the cam end moves the fingers either apart or together as the stem is rotated with the lower arm. Thus, this invention provides a below-the-elbow amputee with a clamping mechanism which can be used to perform a number of tasks. By varying the orientation of the housing relative to the brace and the stem relative to the cuff, the amputee can control the orientation of the fingers as well as the opened and closed positions of the fingers.

What is claimed is:

1. A prosthetic hand, comprising:
   a cuff, said cuff having an open end and a closed end;
   a stem, said stem having a plain end and a cam end, said plain end is attached to said closed end of said cuff;
   a housing pivotally mounted on said stem whereby said stem is free to pivot within said housing, said housing having two opposite sides;
   a first finger pivotally mounted to said housing, said first finger having a first bearing surface and a first clamping end whereby said first bearing surface rides against said cam end of said stem;
   a second finger pivotally mounted to said housing, said second finger having a second bearing surface and a second clamping end whereby said second bearing surface rides against said cam end of said stem;
   means for holding said bearing surfaces of said fingers against said cam end of said stem; and
   a brace attached to said housing for stabilizing said housing whereby said cuff can pivot said stem within said housing moving said first clamping end relative to said second clamping end by action of said cam end rotating against said bearing surfaces.

2. A prosthetic hand as recited in claim 1, wherein said attachment of said plain end of said stem to said cuff, comprises:
   a cylindrical anchor attached to said closed end of said cuff and enclosing said plain end of said stem; and
   a pin, said pin extending from said cylindrical anchor into said plain end of said stem whereby said stem is locked to said cylindrical anchor.

3. A prosthetic hand as recited in claim 1, wherein said attachment of said plain end of said stem to said cuff, comprises:
   a cylindrical anchor attached to said closed end of said cuff and enclosing said plain end of said stem, said cylindrical anchor having a threaded hole; and
   a set screw within said threaded hole of said cylindrical anchor whereby said set screw locks said stem to said cylindrical anchor.

4. A prosthetic hand as recited in claim 1, further comprising roller bearings located between said stem and said housing to facilitate rotation of said stem within said housing.

5. A prosthetic hand as recited in claim 2, further comprising roller bearings located between said cylindrical anchor and said housing to facilitate rotation of said stem within said housing.

6. A prosthetic hand as recited in claim 3, further comprising roller bearings located between said cylindrical anchor and said housing to facilitate rotation of said stem within said housing.

7. A prosthetic hand as recited in claim 1, wherein said clamping ends of said fingers have a roughened surface.

8. A prosthetic hand as recited in claim 1, wherein said means for holding said bearing surfaces of said fingers against said cam end of said stem, comprises an elastic band wrapped around said fingers.

9. A prosthetic hand as recited in claim 1, wherein said brace, comprises:
   a first bar having two ends and also having a pivot between said two ends, one of said two ends is attached to one of said opposite sides of said housing;
   a second bar having two ends and also having a pivot between said two ends, one of said two ends is attached to other said opposite side of said housing whereby said pivot point of said second bar is aligned with said pivot point of said first bar; and
   a strap connected to said other ends of said first and second bars.

10. A prosthetic hand as recited in claim 9, wherein said strap, further comprises an adjustable means fastened to said strap for tightening said strap.

11. A prosthetic hand as recited in claim 10, wherein said adjustable means, comprises a nylon fabric which can be fastened to itself.

12. A prosthetic hand, comprising:
   a cuff, said cuff having an open end and a closed end;
   a cylindrical anchor attached to said closed end of said cuff, said cylindrical anchor having a threaded hole;
   a set screw within said threaded hole of said cylindrical anchor;
   a stem, said stem having a plain end and a cam end, said plain end is inserted within said cylindrical anchor and is locked to said cuff by said set screw;
   a housing pivotally mounted on said cylindrical anchor whereby said stem is free to pivot within said housing, said housing having two opposite sides;
   roller bearings located between said cylindrical anchor and said housing to facilitate rotation of said stem within said housing;
   a first finger pivotally mounted to said housing, said first finger having a first bearing surface and a first clamping end whereby said first bearing surface rides against said cam end of said stem, said first clamping end further having a roughened surface;
   a second finger pivotally mounted to said housing, said second finger having a second bearing surface and a second clamping end whereby said second bearing surface rides against said cam end of said stem, said second clamping end further having a roughened surface;

means for holding said bearing surfaces of said fingers against said cam end of said stem;

a first bar having two ends and also having a pivot between said two ends, one of said two ends is attached to one of said opposite sides of said housing;

a second bar having two ends and also having a pivot between said two ends, one of said two ends is attached to other said opposite side of said housing whereby said pivot point of said second bar is aligned with said pivot point of said first bar;

strap connected to said other ends of said first and second bars; and a nylon fabric which can be fastened to itself is attached to said strap for adjusting size of said strap.

13. A prosthetic hand as recited in claim 12, wherein said means for holding said bearing surfaces of said fingers against said cam end of said stem, comprises an elastic band wrapped around said fingers.

* * * * *